United States Patent [19]

Descas et al.

[11] Patent Number: 5,081,137
[45] Date of Patent: Jan. 14, 1992

[54] AMINO-2 ARYLOXYMETHYL-5 OXAZOLINES, AND THEIR SALTS

[75] Inventors: Patrick Descas, Eysines; Emmanuel Panconi, Merignac; Christian Jarry, Artigues, all of France

[73] Assignee: Laboratoires SARGET, Merignac Cedex, France

[21] Appl. No.: 507,463

[22] Filed: Apr. 11, 1990

[30] Foreign Application Priority Data

Apr. 14, 1989 [FR] France .................. 89 05180

[51] Int. Cl.⁵ .................. A61K 31/42; C07D 263/28
[52] U.S. Cl. .................. 514/377; 548/233
[58] Field of Search .................. 548/233; 514/377

[56] References Cited

U.S. PATENT DOCUMENTS

| | | | |
|---|---|---|---|
| 2,181,085 | 11/1939 | Alquist et al. | 549/559 |
| 2,186,894 | 1/1940 | Brodersen et al. | 548/233 |
| 3,637,726 | 1/1972 | Faith | 548/233 |
| 3,818,028 | 6/1974 | Faith | 548/233 |
| 4,497,812 | 2/1985 | Creuzet et al. | 548/233 |

OTHER PUBLICATIONS

Christian Jarry et al., Synthese Et Etude Structurale D'Amino-2 Oxazolines-2 A Action Antihypertensive, Bull. Soc. Pharm. Bordeaux, vol. 120 (1981), pp. 153-162.

G. Poos et al., Journal of Medicinal Chemistry, vol. 6, May 1963, No. 3, pp. 266-272.

*Primary Examiner*—Donald G. Daus
*Attorney, Agent, or Firm*—Oblon, Spivak, McClelland, Maier & Neustadt

[57] ABSTRACT

The present invention concerns amino-2 aryloxymethyl-5 oxazolines having the structure:

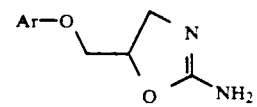

wherein the aryl group Ar is choosen from the group consisting in phenyl-2 phenyl, phenyl-3 and phenyl-4 phenyl. The compounds according to the invention are useful as medicines.

7 Claims, No Drawings

AMINO-2 ARYLOXYMETHYL-5 OXAZOLINES, AND THEIR SALTS

BACKGROUND OF THE INVENTION

The present invention is relative to novel amino-2 aryloxymethyl-5 oxazolines, as well as to their salts with pharmacologically compatibles acids.

The compound according to the invention have the general formula:

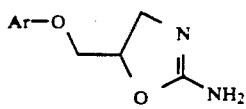

wherein Ar is a phenyl-2 phenyl, phenyl-3 phenyl or phenyl-4 phenyl group.

The compounds according to the invention are prepared by condensation of aryloxy-1 epoxy-2,3 propanes having the structure II

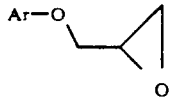

wherein Ar has the same meaning as hereinabove, with a sodium monocyanamide in an organic solvent soluble in water, as the lower alcools in $C_1$ to $C_4$, e.g. methanol, ethanol, isopropanol or butanol, or as tetrahydrofuran or dimethylformamide, and at a temperature between 0° C. and 80° C.

The compounds having structure II are well known, and their preparations are disclosed in U.S. Pat. No. 2,181,085 assigned to DOW CHEMICAL COMPANY.

The Assignee has already disclosed in French patents 2533922 and 2546167 amino-2 aminomethyl-5 oxazolines.

JARRY et al. have disclosed in Bull. Soc. Pharm. Bordeaux. 1981, 120. 153-162 aryloxymethyl-5 amino-2 oxazolines having structure III.

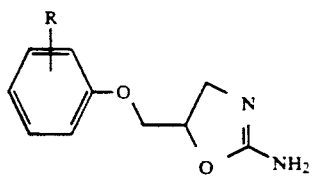

wherein group R is a methyl group in position 4, chlorine in position 4, methoxy in position 4, an acetamido group in position 4, or allyl in position 4 and methoxy in position 2. or group R is a CH=CH-CH=CH group in 2,3 and constitutes with the benzene cycle a naphtyl-1 group. These compounds have interesting antihypertension properties.

DOW CHEMICAL has described in U.S. Pat. No. 3,637,726 assigned to said corporation (dihalo-3,4 phenoxy)methyl-5 amino-2 oxazolines having structure IV

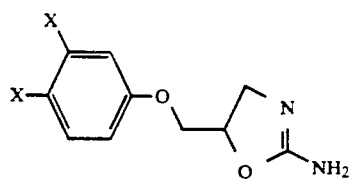

wherein X represents an halogen atom, as chlorine or bromine. These compounds enjoy interesting antimicrobial properties.

DESCRIPTION OF PREFERRED EMBODIMENTS

The invention will now be described more precisely in the following examples which are given without any limiting purpose.

The melting points are measured with a Kofler device, the chemicals displacements are expressed in ppm relatively to the TMS used as internal standard.

EXAMPLE 1

Amino-2 (phenyl-2 phenoxymethyl)-5 oxazoline or COR3264, product having structure I with Ar=phenyl-2 phenyl.

SYNTHESIS

In a flask of 500 cm³, provided with a stirrer and a cooler or condenser, 34 g of (phenyl-2 phenoxy)-1 epoxy-2,3 propane, 150 ml of anhydrous methanol and 11 g of sodium monocyanamide are introduced. The reacting mixture is stirred during 16 hours at the ambient temperature. The mineral salts are filtred on Celite 535. The filtrate is evaporated under vaccum. To the residue are added in 250 ml of chloroform. The solution in chloroform is washed twice with 20 ml of water, dried on sodium sulfate and evaporated under vacuum. The obtained product is recrystallized in heptane. 13g of COR3264 are obtained as a white solid. The output is =31%, the molecular weight is 268.32.

PHYSICO-CHEMICALS PROPERTIES

Melting point 124°

MNR spectrum in $CDCl_3$: 3.2-4.2 ppm, 4 protons, complex hill, 2 $CH_2$; 4.5-5.0 ppm, 3 protons, 1 CHO of oxazoline + $NH_2$ exchangeable with $D_2O$; 6.8-7.7 ppm, 9 protons, complex hill, aromatic protons.

EXAMPLE 2

Amino-2 (phenyl-4 phenoxymethyl)-5 oxazoline or COR4408, product of structure I with Ar=phenyl-4 phenyl.

SYNTHESIS

In a flask of 1500 cm³, provided with a stirrer and a cooler or condenser 55 g of (phenyl-4 phenoxy)-1 epoxy-2,3 propane, dissolved in 800 ml of a mixture of tetrahydrofuran-methanol 50/50, are introduced, then 32 g of sodium monocyanamide are added. The reacting mixture is stirred during 48 hours at ambient temperature. The mineral salts are filtered on Celite 535. The filtrate is evaporated under vaccum. To the residue are added 250 ml of ethyl ether; the solid which precipitated is filtered, then washed with 200 ml of water. The obtained solid is recrystallized in a mixture toluene-methanol and dried under vaccum. 30.5 g of COR4408 are obtained as a white solid. The output is 47%, the molecular weight = 268.32.

PHYSICOCHEMICALS PROPERTIES

Melting point 201°

NMR spectrum in DMSO $D_6$: 3.1–4.3 ppm, 4 protons, complex hill, 2 $CH_2$; 4.5–5.0 ppm, 1 proton, multiplet, 1 CHO of oxazoline; 5.8 ppm, broad peak, 2 protons, $NH_2$ exchangeable with $D_2O$; 6.9–7.7 ppm, 9 protons, complex hill, aromatic protons.

EXAMPLE 3

Amino-2 (phenyl-3 phenoxymethyl)-5 oxazoline or COR4463, product of structure 1 with Ar=phenyl-3 phenyl.

SYNTHESIS

In a flask of 500 cm³, provided with a stirrer and a cooler or condenser, 18 g of sodium monocyanamide in 150 ml of anhydrous methanol are introduced, then 28 g (phenyl-3 phenoxy)-1 epoxy-2,3 propane dissolved in 50 ml of anhydrous methanol are added drop by drop. The reacting mixture is stirred during 16 hours at ambient temperature. The mineral salts are filtered on Celite 535. The filtrate is evaporated under vaccum. 250 ml of dichloromethane are added to the residue. The solution is washed with twice 20 ml of water, dried on sodium sulfate and evaporated under vaccum. The obtained product is recrystallized in heptane. 15 g of COR4463 are obtained as a white solid. Output: 48%, molecular weight: 268.32.

PHYSICOCHEMICALS PROPERTIES

Melting point 124°

NMR spectrum in $CDCl_3$: 3.3–4.3 ppm, 4 protons, complex hill, 2 $CH_2$; 4.6–5.3 ppm, 3 protons, complex hill, 1 CHO of oxazoline + $NH_2$ exchangeable with $D_2O$; 6.7–7.7 ppm, 9 protons, complex hill, aromatic protons.

TOXICOLOGIC PROPERTIES

The acute toxicity of COR3264, COR4408 and COR4463 has been determined on the mouse after oral administration. The DL50 for these three compounds are the following:

1. COR3264 DL50 = 273 mg/kg
2. COR4408 DL50 = 800 mg/kg
3. COR4463 DL50 = 389 mg/kg.

PHARMACOLOGICAL PROPERTIES

The compounds according to the invention have been tested in a psychopharmacological screening. The various tests which has been used are the following:

Measurement of the motorial activity with an Boissier actimeter,

Antagonism relatively to the hypothermy produced by the subcutaneous injection of 2.5 mg/kg of reserpine, Antagonism relatively to the hypothermy produced by the subcutaneous injection of 16 mg/kg of apomorphine, Potentiation of the toxicity by yohimbine, TST, test of suspending the animal by his tail.

All the products have been orally administrated.

In the actimetry test, COR3264 demonstrates no activity up to the dose of 64 mg/kg and produces a slight diminution of the spontaneous motorial activity at the dose of 128 mg/kg; COR4408 demonstrates no activity up to the dose of 64 mg/kg and produces a diminution of the spontaneous motorial activity at the dose of 256 mg/kg; COR4463 is sedative starting at the dose of 16 mg/kg.

The activity relatively to the hypothermy induced by reserpine has been determined on the mouse; COR3264 shows no activity up to the dose of 128 mg/kg; COR4408 has a DE50 of 40 mg/kg; COIR4463 is inactive up to the dose of 128 mg/kg.

The activity relatively to the hypothermy induced by the injection of 16 mg/kg of apomorphine has been determined on the mouse; COR3264 does not show any activity up to the dose of 128 mg/kg; COR4408 has a DE50 of 73 mg/kg COR4463 is inactive up to the dose of 128 mg/kg.

In the test of suspending the animal by the tail an effective dose 25, DE25, has been determined for the three substances: for COR3264 it is of 16 mg/kg, for COR4408 it is of 130 mg/kg and for COR4463 it is of 90 mg/kg.

The potentiation of the toxicity by yohimbine has been determined. The DL50 after administration of 30 mg/kg of yohimbine by sub-cutaneous injection is for COR3264 70 mg/kg, for COR4408 16 mg/kg and for COR4463 37 mg/kg.

The pharmacological results, indicated hereinabove, predict an antidepressive activity of the compounds according to the invention.

Considering their toxicopharmacological activities, the products object of the invention are therefore useful, alone or in association with other active principles, for treating depressive states or conditions.

The doses and the therapeutical treatments depend on the patient and the illness to cure. The products can be administrated orally (e.g. as capsules, pills, syrup, drinkable drops), by injection (e.g. solute injectable by intramuscular or intraveinous administration, solute for intraveinous perfusion), by rectal introduction (suppositories), locally or topicaly (creams, pomades or ointment, gels). According to the indications, the daily dose may vary from 10 to 2000 mg per day in one to four takings.

It will be apparent to those skilled in the art that various variations and modifications could be made to the products of the invention without departing from the scope thereof, as claimed.

We claim:

1. A compound of the formula:

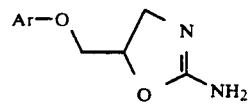

wherein Ar is selected from the group consisting of phenyl-2 phenyl, phenyl-3 phenyl and phenyl-4 phenyl, and pharmaceutically acceptable salts thereof.

2. The compound of claim 1, wherein Ar is phenyl-2 phenyl.

3. The compound of claim 1, wherein Ar is phenyl-3 phenyl.

4. The compound of claim 1, wherein Ar is phenyl-4 phenyl.

5. A pharmaceutical composition comprising a compound of the formula:

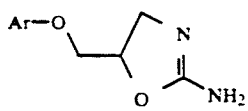

wherein Ar is selected from the group consisting of phenyl-2 phenyl, phenyl-3 phenyl and phenyl-4 phenyl, and pharmaceutically acceptable salts thereof, in an amount effective for the treatment of depression, in a pharmaceutically acceptable carrier.

6. A method for treating depression, comprising administering to a patient in need thereof a compound of the formula:

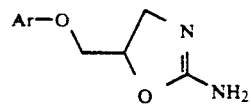

wherein Ar is selected from the group consisting of phenyl-2 phenyl, phenyl-3 phenyl and phenyl-4 phenyl, and pharmaceutically acceptable salts thereof, in an amount effective for the treatment of depression, in a pharmaceutically acceptable carrier.

7. The method of claim 6, wherein said compound is administered to said patient from 1 to 4 times per day, such that an amount of from 10 to 2,000 mg of said compound is administered per day to said patient.

* * * * *